US005695125A

United States Patent [19]

Kumar

[11] Patent Number: 5,695,125

[45] Date of Patent: Dec. 9, 1997

[54] DUAL PRESSURE REGULATOR HAVING BALANCED REGULATOR VALVES SUPPORTED IN SPRAYER HANDLE-CONFORMAL UNIBODY STRUCTURE

[75] Inventor: Viraraghavan S. Kumar, Palm Bay, Fla.

[73] Assignee: Teknocraft, Inc., West Melbourne, Fla.

[21] Appl. No.: 385,913

[22] Filed: Feb. 9, 1995

[51] Int. Cl.$^6$ .............................................. A61M 11/02

[52] U.S. Cl. .............................. 239/364; 239/76; 239/344

[58] Field of Search .............................. 239/76, 337, 364, 239/373, 344, 346

[56] References Cited

U.S. PATENT DOCUMENTS 5,054,687 10/1991 Burns et al. ........................ 239/337 X
5,100,060 3/1992 Haferkorn .............................. 239/337
5,119,992 6/1992 Grime .................................... 239/364

*Primary Examiner*—Brian L. Johnson
*Assistant Examiner*—C. T. Bartz
*Attorney, Agent, or Firm*—Charles E. Wands

[57] ABSTRACT

A dual pressure regulator device for a spray gun is supplied with an input fluid under pressure and outputs a first regulated pneumatic pressure to a pressurized tank, and a second regulated pneumatic pressure to the spray gun. The dual pressure regulator device has a unitary body having a fluid passageway extending from an inlet port at a first end of the body, to which inlet port the input fluid is supplied, to a first valve chamber in which a first regulator valve is installed, and to a second valve chamber in which a second regulator valve is installed. The pressure in the nozzle device's main pressure internal line and the head pressure within the tank are maintained within specified tolerances, independent of pressure fluctuations in the main supply line to the nozzle device. The body has an inclined body wall portion that is conformal with the handle, such that the valve assemblies are physically accommodated and accessible in a space directly beneath the handle, adjacent to the tank.

16 Claims, 4 Drawing Sheets

DUAL PRESSURE REGULATOR HAVING BALANCED REGULATOR VALVES SUPPORTED IN SPRAYER HANDLE-CONFORMAL UNIBODY STRUCTURE

FIELD OF THE INVENTION

The present invention relates in general to controlled fluid delivery systems, and is particularly directed to a new and improved dual pressure regulator architecture, having a unibody structure that is configured to be readily conformally attached to the main pressure inlet port at the base of the handle of a hand-held spray apparatus, and which employs balanced regulator valves for maintaining the pressure in the sprayer's main pressure internal line and the head pressure within a liquid storage tank within specified tolerances, independent of pressure fluctuations in the main supply line feeding the sprayer.

BACKGROUND OF THE INVENTION

Hand-held spray devices are used in a variety of utility applications for the delivery of material, such a fine solid particulate matter, and fluid or liquid substances, such as paints, liquid chemicals, and the like, that are capable of being atomized and directed through a spray emission control nozzle onto a given target area. As diagrammatically illustrated in FIG. 1, such a device customarily comprises a hand-held spray gun unit 11 having a 'pistol grip' 13, which an operator uses to both seize the spray gun and operate a trigger mechanism 15, for controlling the emission of a material from a nozzle element 17. The spray pattern delivered by the nozzle element 17 is controlled by a rotatable wheel 19 mounted at the rear of the spray gun unit.

Adjacent to (beneath) the nozzle element 17 is a storage container attachment fitting 21, through which a storage container or tank 23, usually in the form of a metallic or non-metallic bottle or the like, is joined with the spray gun unit 11. The tank 23 is usually pressurized and its contents are drawn into an internal delivery line (not shown) within the spray gun unit ported to the nozzle element 17. To pressurize the contents of the storage container, its top or lid portion 25 is fitted with a pressure port 27, to which a pressurizing fluid (pneumatic) line 29 is attached, in order to establish a prescribed 'head' pressure above the material (e.g. liquid) in the container 23.

For this purpose, the spray gun may be fitted with a pressure valve arrangement, shown at 30, which is installed as an add-on device in a main (pneumatic) pressure inlet line 31. Inlet line is connected in fluid communication with the internal delivery line of the spray gun via an attachment at inlet port 32 at the base of pistol grip handle 13. To set the head pressure in the storage tank 23, the pressure valve arrangement 30 includes a first, head pressure regulator valve 33, having an inlet port 34 coupled to inlet line 31 and an output port 35 coupled to pressure line 29.

Pressure valve arrangement 30 also includes a main pressure regulator valve 37, having an inlet port 36 that is also coupled to the main line 31, and an output port 38 which is coupled directly to the main pressure inlet port 32 at the base of the spray gun handle, so as to set the spray nozzle emission control pressure. For a typical industrial paint spray application, such as an automobile body repair facility, the nozzle pressure may be on the order of 100 psi, while the head pressure within the storage container is considerably reduced relative to that of the main supply and may be on the order of only 10 psi.

For precision industrial applications, it is critical that the spray emission be maintained within a given tolerance, in order to ensure the proper application and coverage of the delivered material (e.g. paint) on the target surface. For the example of an auto body repair facility, since a painted replacement or repaired area should match the original paint of the remainder of the vehicle, maintaining control pressures for the paint sprayer within given tolerances for achieving matching, uniform coverage is essential.

Unfortunately, it has been found that the pressure valve arrangement shown in FIG. 1 suffers from a number of shortcomings. First of all, simply porting a head pressure control valve to the main supply line will not necessarily maintain the desired storage tank head pressure. The problem is the fact that operation of the paint sprayer gun trigger causes the pressure in the main line, to which the storage tank is ported, to drop, thereby causing a fluctuation in the head pressure, which is sourced to the main line pressure. Secondly, the physical configuration of the valve arrangement at the base of the sprayer handle does not lend itself to ease of use, since the operator typically holds the sprayer handle with his arm extended and wrist cocked downwardly. Simply connecting a pair of discrete valve units together at the base of the pistol grip handle means that the operator now has to deal with a 'kluge'-like structure that impedes arm and wrist movement.

SUMMARY OF THE INVENTION

In accordance with the present invention, the need to maintain a prescribed storage tank head pressure tolerance, without resorting to a regulator valve configuration that is both functionally inadequate and constricts the movement of the sprayer by the operator, is readily accomplished by means of a conformal unibody structure that contains a pair of balanced pressure regulator valves. The conformal dual pressure regulator valve architecture of the present invention is attachable to the main pressure inlet port at the base of the handle of a hand-held spray gun, such as an industrial paint sprayer, and employs balanced regulator valves for maintaining the pressure in the sprayer's main pressure internal line and the head pressure within the liquid storage tank within specified tolerances, independent of pressure fluctuations in the main supply line to the sprayer.

For this purpose, the dual valve structure may comprise a plastic body having a threaded inlet port bored into a first end surface, which is sized to receive a complementarily externally threaded main supply line fixture. An internal fluid supply line extends at an acute angle from the inlet port and is intersected by a first valve chamber in which a first balanced, regulator valve is installed, and terminates at a second valve chamber in which a second balanced, regulator valve is installed. The first valve chamber is connected to a first threaded outlet port for connection to the head pressure supply line, while the second valve chamber is connected to a second threaded outlet port for connection to the main supply line inlet port at the base of the spray gun handle.

The external surface of the body has a flat bottom surface portion that extends toward the first flat endwall surface and an inclined body wall portion that extends between the flat bottom surface portion and the first endwall surface and is generally parallel to the internal fluid supply bore. A first flat top surface portion extends from a body end surface containing the second outlet port and terminates at a vertical wall or step portion that is generally parallel to each of endwall surfaces. The vertical wall portion terminates at a second flat top surface portion which extends to the first endwall surface.

The differential height between the first and second flat top surface portions relative to the distance between the first and second valve chambers defines a slope that is parallel to that of the inclined body wall portion. This sloped offset of valve chambers provides room for the valve assemblies, including their associated control knobs, to be physically accommodated and accessible in a space underneath the pistol grip handle, that is immediately adjacent to the spray material storage container.

Those portions of the body where the first and second valve chambers are located have a generally hexagonal outer surface. This facilitates stabilizing the body during installation of the valve components, and permits valve output port fittings to be mounted at a variety of orientations, so that the head pressure supply line may be oriented so as to maintain a generally smooth contour from the head pressure regulator valve output port to the fitting at the top of the spray gun storage container. Each of the two balanced regulator valves, per se, is of conventional construction, and is threaded into an internally threaded bore of a respective valve chamber.

DETAILED DESCRIPTION

As noted briefly above, the dual pressure regulator valve device of the present invention employs an 'operator-friendly', conformal unibody structure, that is attachable to the base of the handle of a hand-held spray apparatus, and contains a pair of balanced regulator valves, which are operative to maintain the pressure in the sprayer's main pressure internal line and the head pressure within the liquid storage tank within specified tolerances independent of pressure fluctuations in the main supply line to the sprayer.

Figure 2:
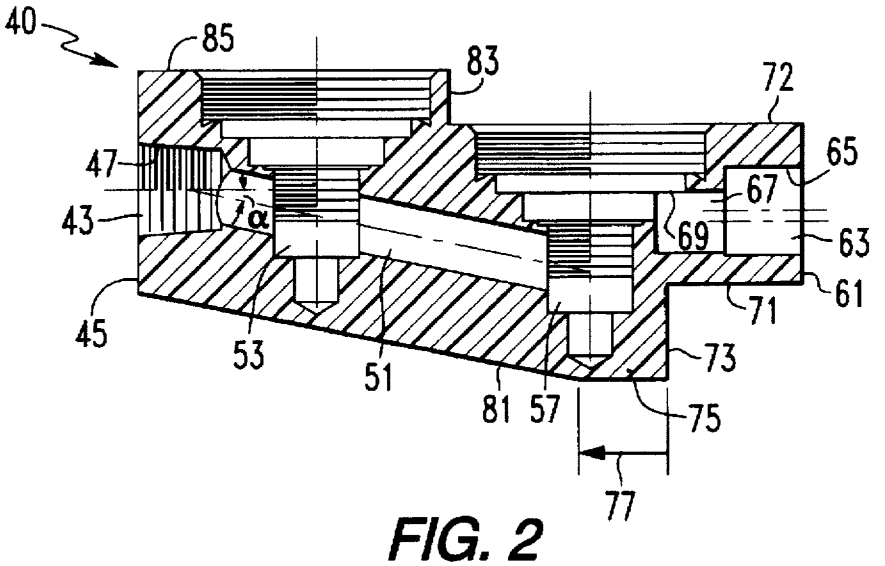
FIG. 2 diagrammatically shows the overall unitary body structure of the dual valve architecture of the present invention.

Referring now to FIG. 2, the overall unitary body structure of the dual valve architecture of the present invention is shown in a side sectional view as comprising a unitary body 40, having an inlet port 43 bored into a first, generally flat end surface 45 of the body. As a non-limiting example, body 40 may comprise a plastic (e.g. polystyrene) material. Inlet port 43 is generally cylindrically configured and has an internally threaded surface 47 that is sized to receive a complementarily externally threaded fixture for attachment to the main pneumatic supply line for operating the sprayer. Extending at an acute angle $\alpha$ from inlet port 43 is an internal fluid supply bore 51, which intersects a first valve chamber 53, in which a first balanced, regulator valve is installed, and terminates at a second valve chamber 57, in which a second balanced, regulator valve is installed. Each of the balanced valves is shown in detail FIG. 5, to be described.

Figure 3:
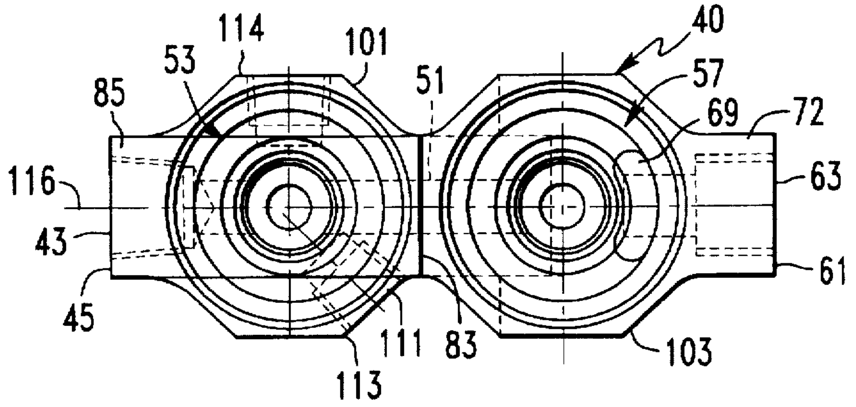
FIGS. 3 and 4 are respective top and bottom plan views of the unitary body structure of the dual valve architecture shown in FIG. 2.
Figure 4:
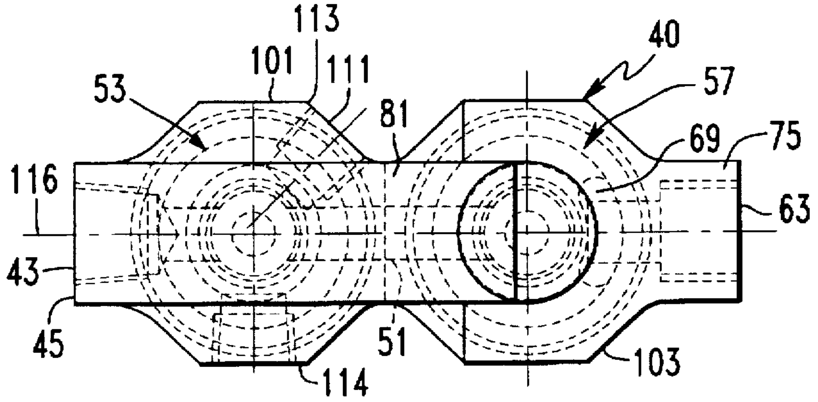

Body 40 has a second, generally flat end surface 61 from which a main supply line outlet port 63 is ported. Outlet port 63 is also generally cylindrically configured and has an internally threaded surface 65 that is sized to be threaded onto a complementarily externally threaded fixture, corresponding to port 32 at the base of the pistol grip handle of the sprayer device, such as that shown in FIG. 1, described above. Outlet port 63 is coupled through a bore 67 to an outlet port 69 of the second valve chamber 57. (The outlet port for the first valve chamber 53, to be described with reference to FIGS. 3 and 4, is not shown in FIG. 2.)

Extending from end surface 61 of body 40 is a first base wall portion 71, which terminates at a first vertical wall portion 73, that is generally parallel to each of endwall surfaces 45 and 61. First vertical wall portion 73 terminates at a flat bottom surface portion 75, that extends a prescribed distance 77 toward the first endwall surface 45. An inclined wall portion 81 extends between flat bottom surface portion 75 and first endwall surface 45, and is generally parallel to internal fluid supply bore 51.

Also extending from end surface 61 is a second base wall portion 72, which terminates at a first vertical step portion 83, that is generally parallel to each of endwall surfaces 45 and 61. The vertical step portion 83 terminates at a first flat, top surface portion 85, that extends to the first endwall surface 45.

The differential height of the second flat top surface portion 91 and the first flat top portion 85 relative to the distance between the first and second valve chambers 53 and 57 defines a slope corresponding to that of the inclined body wall portion 81 between the flat bottom surface portion 75 and first endwall surface 45. As noted above, and as is diagrammatically illustrated in FIG. 7, to be described, this sloped offset of the valve chambers provides room for the valve assemblies, including their associated control knobs, to be physically accommodated and accessible in a space underneath the pistol grip handle, that is immediately adjacent to the spray material storage container.

As shown in the plan views of FIGS. 3 and 4, those portions of the body 40 where the first and second valve chambers 53 and 57 are located have a generally hexagonal surface contour, as shown at 101 and 103. The hexagonal shape of these body portions 101 and 103 facilitates stabilizing the body during installation of the valve components, and enables valve output port fittings to be mounted at a variety of orientations, so that the head pressure supply line may be oriented so as to maintain a generally smooth contour from the head pressure regulator valve output port to the fitting at the top of the spray gun storage container.

More particularly, as a non-limiting example, hexagonal surface body portion 101 has a wall region 113 oriented at an acute angle (60°) relative to a longitudinal axis 116 of the body 40, axis 116 being generally parallel to the axis of outlet port 69 of the second valve chamber 57. The first valve chamber 53 is shown as having an output port 111 that extends from wall region 113 to the interior of valve chamber 53. (Alternatively, the first valve chamber output port may extend to another surface region, as shown at 114.) For the 60° orientation of wall region 113, when the dual pressure regulator valve body 40 is mounted to the lower end of the sprayer handle, output port 111 of the first valve chamber 53 faces generally upwardly toward the top of the liquid storage tank, thereby facilitating the connection of a fitting of the head pressure supply line and maintaining a generally smooth contour of the head pressure supply line from the head pressure regulator valve and the fitting at the top of the liquid storage tank.

Although each of the two balanced regulator valves, per se, is of conventional construction, the assembly of each valve and the manner in which the valves are installed in the body to form an integrated unit will be described. As is shown in the sectional view of FIG. 5, each regulator valve has an upper valve body member 121, a lower end of which has an externally threaded, generally cylindrically configured base portion 123, which is sized to be threaded into an internally threaded bore 125 of a respective valve chamber (shown separately detail in FIG. 6).

Upper valve body member 121 has an interior chamber 131, an upper portion 133 of which has an interior hexagonal surface 135 sized to receive a hexagonal nut fitting 137 that is threaded onto a cylindrical shaft 139. The upper end 140 of shaft 139 has a fitting 141, which is engagable by an interior shaft element 143 of a lockable, rotatable adjustment knob 145. Pulling the knob 145 upwardly unlocks the position of the hexagonal nut fitting 137 and allows the fitting 137 to be axially displaced, and thereby change the effective length and the effective spring force imparted by a compression spring 147 that is placed upon shaft 139, so as to be is captured between a washer 151 at the lower surface 138 of hexagonal nut fitting 137 and a washer 153 placed upon a bottom interior surface portion 155 of a generally circular diaphragm cup member 157, which is coaxial with the axis 144 of shaft 139. When the knob 145 is pushed down it locks the position of the hexagonal nut fitting 137 and prevents the fitting 137 from being axially displaced. This sets the effective length and thereby the effective spring force imparted by the compression spring 147 against the bottom interior surface portion 155 of diaphragm cup member 157.

The diaphragm cup member 157 is attached to a diaphragm disk member 161, the outer peripheral portion 163 of which is seated at the bottom interior rim portion 165 of threaded bore 125. Communicating with threaded bore 125 is a coaxial cylindrical diaphragm chamber 171, which opens into a generally cylindrical and coaxial valve port depression 173 that is in fluid communication with the valve's output port. Diaphragm disk member 161 is captured on a lower T-shaped cylindrical fitting 175, a leg portion 177 of which passes through washer 153 and receives the lower end of the compression spring 147, and has an axial bore 181. A T-portion 179 of fitting 175 has an axial bore 183, of a diameter larger than that of bore 181 and sized to receive a solid axial pin 185. Pin 185 passes through a bore 187 in a web portion 188 of a lower valve T-shaped cup member 191.

Lower valve T-shaped cup member 191 has a threaded cylindrical body portion 192 that is threaded into complementary threads 193 of a valve chamber bore 194 that extends from the annular ledge portion 174 of the cylindrical valve port depression 173 to a lower cylindrical bore 196, which is sized to receive a spool member 200. Valve chamber bore 194 intersects internal fluid supply bore 51.

T-shaped cup member 191 has a circular rim portion 195 that is sized to fit within and abut against an annular ledge portion 174 of the cylindrical valve port depression 173. T-shaped cup member 191 also has a larger diameter interior bore 201 that is coextensive with an upper cylindrical depression 203 in cylindrical spool member 200. An O-ring 213 is captured in a circular groove 215 in the outer cylindrical surface 217 of spool 200, so as to provide a seal between the spool 200 and the lower cylindrical bore 196.

A compression spring 221 is captured between the bottom surface 223 of valve chamber bore 194 and a bottom surface 225 of a T body portion 227 of spool 200. The T body portion 227 of spool 200 has a top surface annular groove 231, in which an O-ring 233 is inserted. When T-shaped cup member 191 is threaded into valve chamber bore 194, its lower surface is urged against O-ring 223, and causes downward displacement of spool 200, so that compression spring 221 is compressed, setting an initial output port pressure.

Spool 200 has an axial bore 241 that extends from bottom spool surface 243 to a cylindrical slot 245 in which pin 185 is inserted. A lower portion 247 of pin 185 has an axial bore 249 that is in fluid communication with axial bore 241 of spool 200 and terminates at radial holes 251. Radial holes 251 provide fluid communication between axial bore 249 of pin 185 and interior bore 201 of T-shaped cup member 191, which opens into the cylindrical valve port depression.

Figure 5:
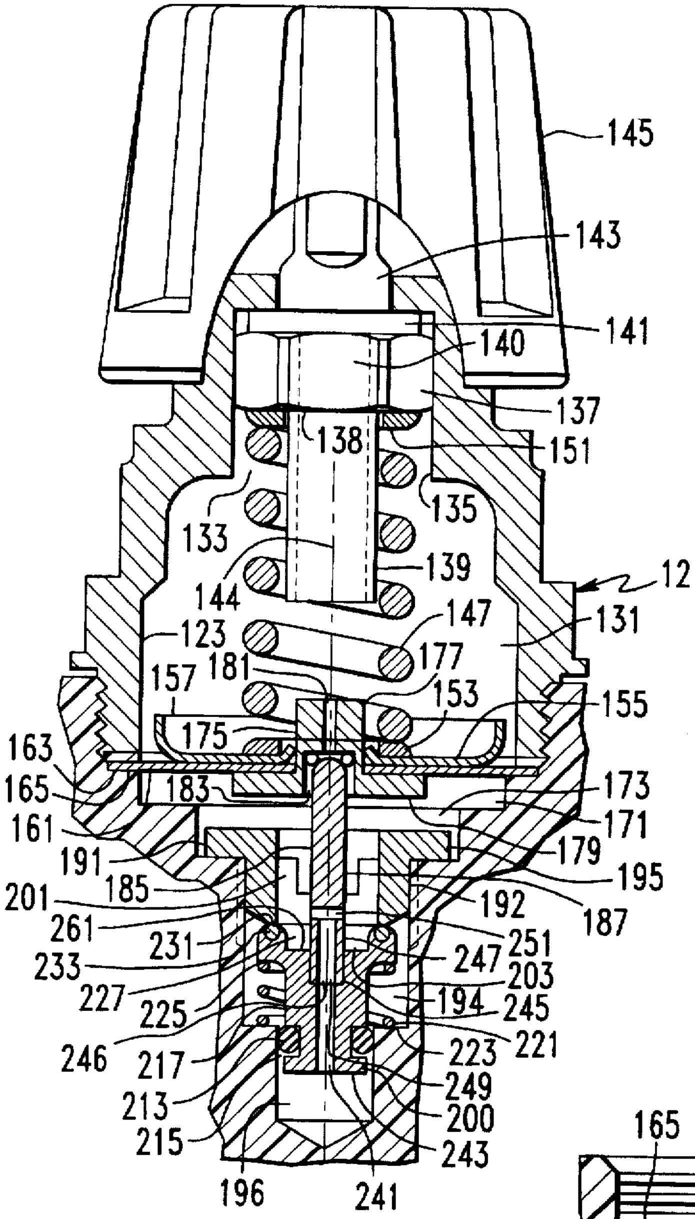
FIG. 5 is a detailed sectional view of the assembly and installation of a respective balanced regulator valve in the architecture of FIG. 2.
Figure 6:
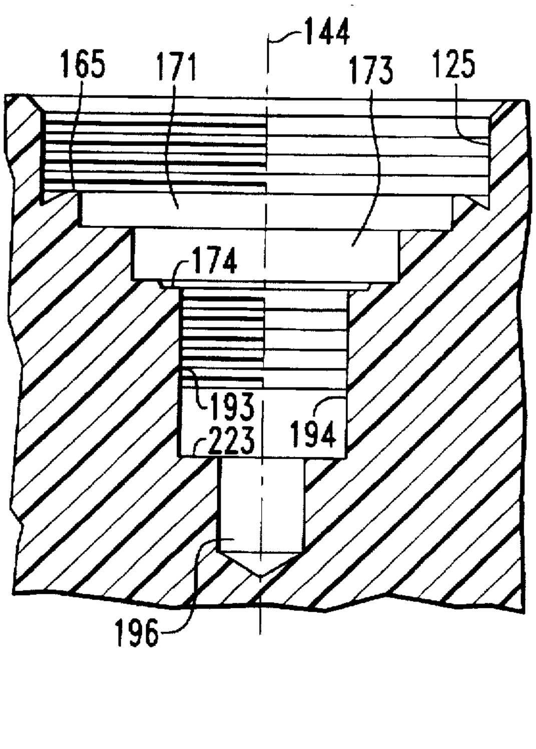
FIG. 6 shows the configuration of a respective valve chamber.

As pointed out above, because the configuration of the regulator valve structure of FIG. 5, is balanced, the valve maintains a given output port pressure independent of pressure fluctuations in the main supply line 51. This balance is obtained by the products of fluid pressure times the effective areas of the upper and lower surfaces of spool 200. The desired output port pressure is established by rotating the control knob 145 until the force imparted by compression spring 147 against diaphragm cup member 157. This force, in turn, axially displaces pin 185, against the bottom 246 of cylindrical slot 245 of spool 200 in which pin 185 is inserted, and thereby against the upward bias of compression spring 221. As the pin 185 is urged downwardly against spool 200, spool 200 separates from T-shaped cup member 191, so that the main supply fluid in line 51 flows through bore 201 and into cylindrical valve port depression 173.

Fluid pressure in the outlet acts downwardly upon the central circular land area 261 of the top of spool 200. The product of this pressure and the area 261 is effectively counter-balanced by the product of the circular area of the bottom spool surface 243 and the output port pressure. The output port pressure is coupled from the cylindrical valve port depression 173, through interior bore 201 of T-shaped cup member 191, radial holes 251 and axial bore 249 of pin 185, and then to the lower cylindrical bore 196, in which the spool 200 is inserted.

Figure 1:
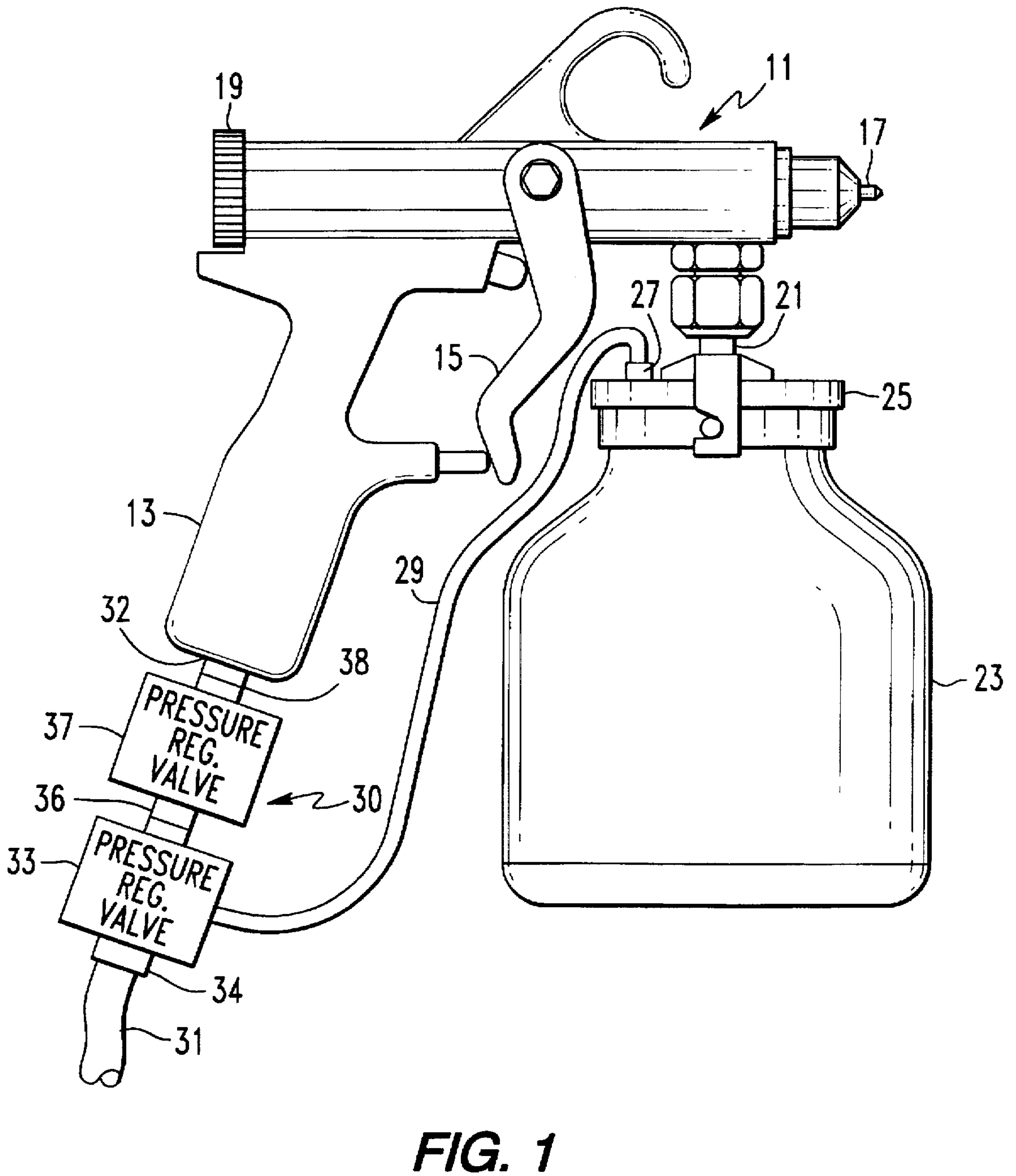
FIG. 1 PRIOR ART
FIG. 1 diagrammatically illustrates a conventional hand-held sprayer device having a pistol grip handle to which a pair of pressure regulator valves are attached.
Figure 7:
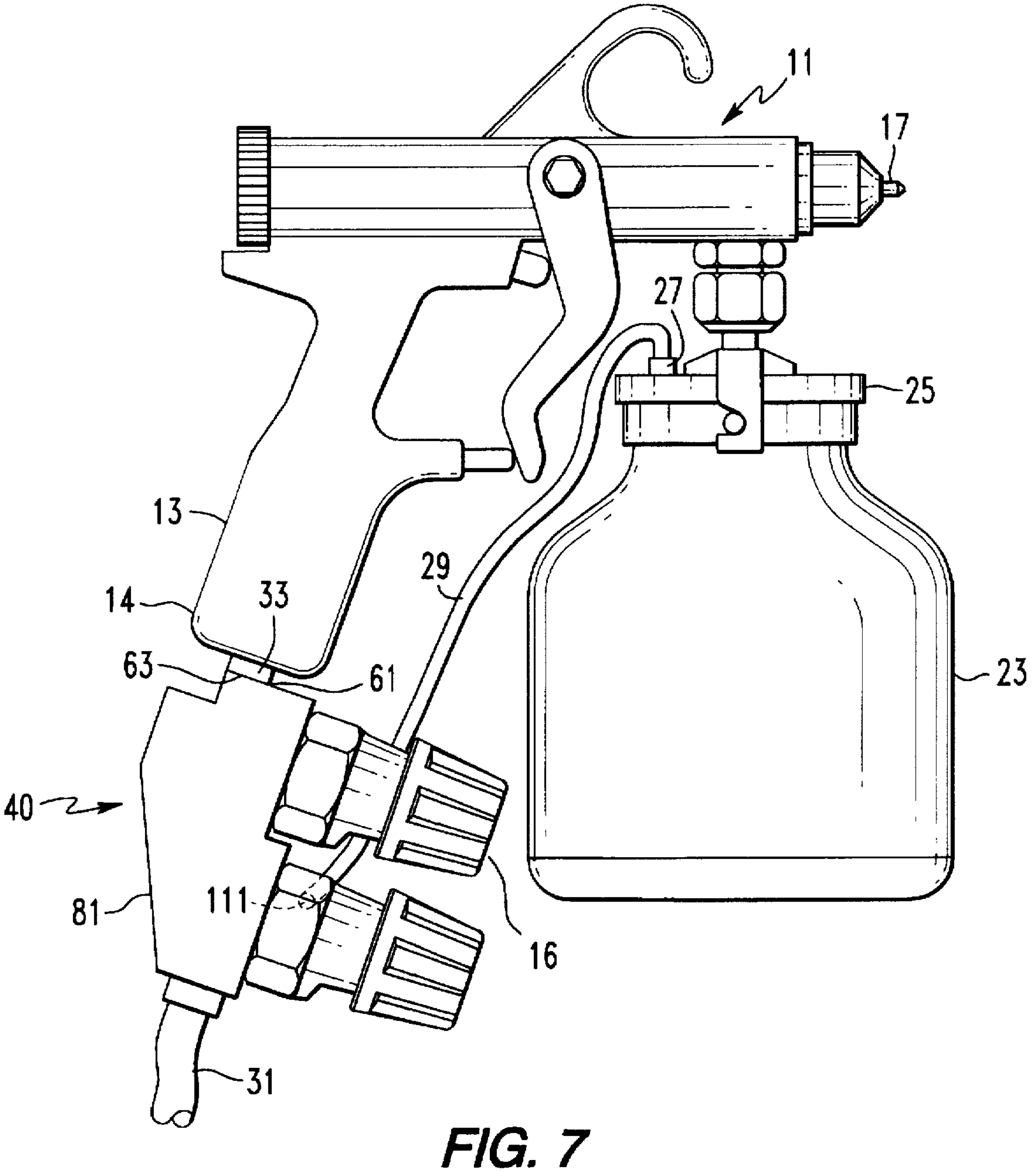
FIG. 7 diagrammatically illustrates the manner in which the dual pressure regulator architecture of the present invention is attached a hand-held spray gun unit.

FIG. 7 diagrammatically illustrates the manner in which the dual pressure regulator architecture of the present invention is attached a hand-held spray gun unit, such as that shown in FIG. 1, described above. As shown, unibody outlet port 63 at the second end surface 61 of the body 40 is coupled to the main supply line inlet port 33 at the base of the pistol grip 13. The regulator body 40 is oriented such that the inclined body wall portion 81 is conformal with the top 14 of handle grip 13, so that the two valve assemblies are physically accommodated and accessible in a space 16 directly beneath the pistol grip handle, adjacent to the spray material storage container 23. Unlike the conventional arrangement of FIG. 1, this conformal physical configuration of the valve arrangement at the base of the sprayer handle readily lends itself to ease of use by an operator holding the sprayer handle with his arm extended and wrist cocked downwardly.

For providing head pressure to the storage tank 23, outlet port 111 is coupled via pressurizing fluid line 29 to the pressure port 27 at the lid portion 25 for pressurizing the contents of the storage container. As noted above, with output port surface region 113 of the first valve chamber 53 facing in a generally upward direction toward the storage tank lid 25, the contour of the pressure supply line is generally smooth, so as to avoid an undesirable 'kink' in the line.

As will be appreciated from the foregoing description, the need to maintain a prescribed storage tank head pressure tolerance, without resorting to a regulator valve configuration that is both functionally inadequate and constricts the movement of the sprayer by the operator, is readily accomplished in accordance with conformal unibody structure dual pressure regulator architecture of the present invention, which employs balanced regulator valves for maintaining the pressure in the sprayer's main pressure internal line and the head pressure within the liquid storage tank within specified tolerances, independent of pressure fluctuations in the main supply line to the sprayer.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein but intend to cover all such changes and modifications as are obvious to one of ordinary skill in the art.

What is claimed:

1. A dual pressure regulator device for receiving an input fluid under pressure and supplying output fluid at a first regulated pressure to a pressurized container which stores a material to be delivered under pressure through a controlled nozzle device, and for supplying output fluid at a second regulated pressure to said controlled nozzle device, said dual pressure regulator device comprising a fluid passageway having an inlet port to which said input fluid is supplied, a first, balanced regulator valve having a first input port coupled to said fluid passageway and a first output port arranged to be coupled to said pressurized container, said first, balanced regulator valve being operative to supply output fluid from said first output port at said first regulated pressure, and a second regulator valve having a second input port coupled to said fluid passageway and a second output port arranged to be coupled to said controlled nozzle device, said second regulator valve being operative to supply output fluid from said second output port at said second regulated pressure, and further comprising a body having said fluid passageway extending therethrough from said inlet port to a first valve chamber in which said first regulator valve is installed, and to a second valve chamber in which said second regulator valve is installed, said first valve chamber being in fluid communication with said first output port at a first location of said body, and said second valve chamber being in fluid communication with said second output port at a second location of said body.

2. A dual pressure regulator device according to claim 1, wherein said second regulator valve comprises a balanced regulator valve.

3. A dual pressure regulator device according to claim 1, wherein said second output port has a first cylindrical axis, and said fluid passageway has a longitudinal axis that is non-parallel to said first cylindrical axis.

4. A dual pressure regulator device according to claim 3, wherein said body has a first end containing said inlet port, a second end containing said second output port, and an outer surface therebetween which is non-parallel to said first cylindrical axis, such that, with said dual regulator device being mounted to a handle of said controlled nozzle device by way of said second output port, said outer surface of said body will be parallel to an outer surface of said handle.

5. A dual pressure regulator device according to claim 3, wherein said first output port has a second cylindrical axis to which said longitudinal axis is non-parallel.

6. A dual pressure regulator device according to claim 1, wherein said inlet port has a first cylindrical axis, said fluid passageway has a longitudinal axis that is non-parallel to said first cylindrical axis, and said second output port has a second cylindrical axis with which said longitudinal axis is non-parallel.

7. A dual pressure regulator device for receiving an input fluid under pressure and supplying output fluid at a first regulated pressure to a pressurized container which stores a material to be delivered under pressure through a controlled nozzle device, and for supplying output fluid at a second regulated pressure to said controlled nozzle device, said controlled nozzle device having a handle which is seized by the hand of an operator, said dual pressure regulator device comprising a unitary body having a fluid passageway extending from an inlet port at first end of said body, to which inlet port said input fluid is supplied, to a first valve chamber in which a first regulator valve is installed, and to a second valve chamber in which a second regulator valve is installed, said first valve chamber being in fluid communication with a first output port at a first location of said body, and said second valve chamber being in fluid communication with a second output port at a second end of said body, said first regulator valve being operative to supply output fluid from said first output port at said first regulated pressure, and said second regulator valve being operative to supply output fluid from said second output port at said second regulated pressure, such the pressure in the nozzle device's main pressure internal line and the head pressure within said pressurized container are maintained within specified tolerances, independent of pressure fluctuations in the main supply line to the nozzle device.

8. A dual pressure regulator device according to claim 7, wherein said body has an inclined body wall portion that is conformal with said handle grip, such that said valve assemblies are physically accommodated and accessible in a space directly beneath said handle, adjacent to said pressurized container.

9. A dual pressure regulator device for receiving an input fluid under pressure and supplying output fluid at a first regulated pressure to a pressurized container which stores a material to be delivered under pressure through a controlled nozzle device, and for supplying output fluid at a second regulated pressure to said controlled nozzle device, said controlled nozzle device having a handle which is seized by the hand of an operator, said dual pressure regulator device comprising a unitary body having a fluid passageway extending from an inlet port at a first end of said body, to which inlet port said input fluid is supplied, to a first valve chamber in which a first balanced, regulator valve is installed, and to a second valve chamber in which a second regulator valve is installed, said first valve chamber being in fluid communication with a first output port at a first location of said body, and said second valve chamber being in fluid communication with a second output port at a second end of said body, said first balanced regulator valve being operative to supply output fluid from said first output port at said first regulated pressure, and said second regulator valve being operative to supply output fluid from said second output port at said second regulated pressure.

10. A dual pressure regulator device according to claim 9, wherein said second regulator valve comprises a balanced regulator valve.

11. A dual pressure regulator device according to claim 9, wherein said unitary body has an outer surface between said first and second ends thereof, said outer surface of said unitary body being configured to be generally conformal with an outer surface of said handle, when said unitary body is connected with said handle by way of said second end thereof.

12. A dual pressure regulator device according to claim 11, wherein said second output port has a first cylindrical axis, and said fluid passageway has a longitudinal axis that is non-parallel to said first cylindrical axis.

13. A dual pressure regulator device according to claim 12, wherein said first output port has a second cylindrical axis to which said longitudinal axis is non-parallel.

14. A dual pressure regulator device according to claim 11, wherein said first inlet port has a first cylindrical axis, said fluid passageway has a longitudinal axis that is non-parallel to said first cylindrical axis, and said second output port has a second cylindrical axis with which said longitudinal axis is non-parallel.

15. A dual pressure regulator device according to claim 14, wherein said fluid passageway has a longitudinal axis that is generally parallel to said outer surface of said unitary body.

16. A dual pressure regulator device according to claim 15, wherein said first and second valve chambers are offset from one another along a line that is generally parallel to said longitudinal axis.

* * * * *